(12) United States Patent
Michaeli

(10) Patent No.: US 6,812,239 B2
(45) Date of Patent: Nov. 2, 2004

(54) METHOD OF IDENTIFICATION OF INHIBITORS OF PDE1C AND METHODS OF TREATMENT OF DIABETES

(75) Inventor: Tamar H. Michaeli, Bronx, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 33 days.

(21) Appl. No.: 10/085,849

(22) Filed: Feb. 27, 2002

(65) Prior Publication Data

US 2002/0160939 A1 Oct. 31, 2002

Related U.S. Application Data

(63) Continuation of application No. 09/245,169, filed on Feb. 5, 1999, now Pat. No. 6,417,208.

(51) Int. Cl.$^7$ ................................................ A01N 43/64
(52) U.S. Cl. ........................................ 514/359; 514/866
(58) Field of Search ................................ 514/359, 866, 514/349

(56) References Cited

U.S. PATENT DOCUMENTS

| | | | | |
|---|---|---|---|---|
| 4,017,539 A | * | 4/1977 | Bosies et al. ............... | 564/233 |
| 5,521,191 A | * | 5/1996 | Greenwald | |
| 5,763,396 A | * | 6/1998 | Weiner et al. ................. | 514/3 |
| 6,056,977 A | * | 5/2000 | Bhagwat et al. ............ | 424/488 |

FOREIGN PATENT DOCUMENTS

WO    WO 97/05876    *  2/1997

OTHER PUBLICATIONS

Parker JC et al., Biochemical and Biophysical Research Communications, 1997, 236(3): 665–669. Modulation of insulin secretion and glycemia by selective inhibition of cyclic AMP phosphodiesterase III.*
Clarke WR et al., Pulmonary Pharmacology, 1994, 7:81–89. The type III phosphodiesterase inhibitor milrinone and type V PDE inhibitor dipyridamole individually and synergistically reduce elevated pulmonary vascular resistance.*
Kohnert et al., Molecular and Cellular Endocrinology (1982), 28: 425–437. Effects of 3–isobutyl–1–methylxanthine of neonatal tissue pancreatic islets maintained in tissue culture.*

Ammala, et al. (1193) Nature 363, 356–358.
Bolaffi, et al. (1990) Endocrinology 126, 1750–1755.
Bornfeldt, et al. (1998) J. Clin, Inves. 102, 869–873.
D'Ambra, et al. (1990) Endocrinology 126, 2815–2822.
D, et al. (1994) Endocrinology 134, 42–47.
El–Metwally, et al. (1997) Eur. J. Pharmacol. 324:227–32.
German, M.S. (1993) Proc. Natl. Acad. Sci. USA 90, 1781–1785.
Grodsky, et al. (1992) J. Cell Biochem. 48, 3–11.
Henquin, et al. (1984) Endocrinology 115, 1125–1134.
Leibowitz, et al. (1995) Diabetes 44:67–74.
Leiser, et al. (1996) Diabetes 45, 1412–1418.
Lester, et al. (1997) Proc. Natl. Acad. Sci. USA 94, 14942–14947.
Liang, et al. (1994) Annu. Rev. Nutr. 14, 59–81.
Lipson, et al. (1983) Life Sci. 32, 775–780.
Newgard, et al. (1995) Annu. Rev. Biochem. 64, 689–719.
Parker, et al. (1995) Biochem. Biophys. Res. Commun. 217:916–23.
Parker, et al. (1997) Biochem. Biophys. Res. Commun. 236:665–9.
Shafiee–Nick, et al. (1995) Br. J. Pharmacol. 115:1486–92.
Thorens, et al. (1996) J. Biol. Chem. 271, 8075–8081.
Zhao, et al. (1997) Proc. Natl. Acad. Sci. USA 94:323–8.

* cited by examiner

Primary Examiner—Christopher R. Tate
Assistant Examiner—Michele C. Flood
(74) Attorney, Agent, or Firm—Amster, Rothstein & Ebenstein LLP

(57) ABSTRACT

The present invention provides a method of identifying novel agents that increase glucose dependent insulin secretion in pancreatic islet cells as well as methods of treating diabetes using the agents which have an inhibitory effect on the activity of pancreatic islet cell phosphodiesterases ("PDE") enzyme, namely PDE1C. The methods described herein are based upon the inventor's surprising discovery that inhibition of PDE1C increases glucose dependent insulin secretion. Specifically, the present invention provides for a method of identifying therapeutic agents that act to increase the release of insulin from pancreatic islet cells. The method of identification provided herein is used to determine the effects of isozyme specific phosphodiesterase inhibitors on insulin secretion from cultured pancreatic β-cells. Also provided are agents that have an inhibitory effect on the activity of PDE1C in pancreatic cells. Further provided is a method of treating diabetes comprising administering to a subject an amount of a PDE1C inhibitor effective to treat the type II diabetes.

9 Claims, 5 Drawing Sheets

```
ACAGGGCAGA GGAGATCAAG TTTGAACAGC ATCAACTCAT
CAGATGAAAG CGATCCGGTG TCAAGAGTTC TGGGTCAGAT
GGAAGTGCTC CCATCAACAA TTCTGTCATT CCTGTTGACT
ATAAGAGTTT TAAAGCCACT TGGACTGAGG TGGTGCAGAT
CAATCGGGAG CGGTGGCGAG CCAAGGTACC CAAAGAAGAA
AAAGCCAAGA AGGAAGCTGA AGAGAAGGCT CGCCTGGCTG
CTGAGGAAAA GCAAAAGGAA ATGGAAGCCA AAAGCCAAGC
TGAACAAGGC ACAACCAGCA AAGGCGAGAA AAAGACATCA
GGAGAAGCCA AAAGTCAAGT CAATGGAACA CGCAAGGGTG
ATAACCCTCG TGGGAAGAAC TCCAAAGGAG AAAAGGCAGG
CGAAAAG
```

FIG. 5

SEQUENCE LISTING

<160> NUMBER OF SEQ ID NOS: 7

<210> SEQ ID NO 1
<211> LENGTH: 407
<212> TYPE: DNA
<213> ORGANISM: Mus musculus

<400> SEQUENCE: 1

```
acagggcaga ggagatcaag tttgaacagc atcaactcat cagatgaaag cgatccggtg    60
tcaagagttc tgggtcagat ggaagtgctc ccatcaacaa ttctgtcatt cctgttgact   120
ataagagttt taaagccact tggactgagg tggtgcagat caatcgggag cggtggcgag   180
ccaaggtacc caaagaagaa aaagccaaga aggaagctga agagaaggct cgcctggctg   240
ctgaggaaaa gcaaaaggaa atggaagcca aagccaagc tgaacaaggc acaaccagca    300
aaggcgagaa aaagacatca ggagaagcca aagtcaagt caatggaaca cgcaagggtg    360
ataaccctcg tgggaagaac tccaaaggag aaaaggcagg cgaaaag                 407
```

<210> SEQ ID NO 2
<211> LENGTH: 23
<212> TYPE: DNA
<213> ORGANISM: Mus musculus

<400> SEQUENCE: 2

```
acagggcaga ggagatcaag ttt                                            23
```

<210> SEQ ID NO 3
<211> LENGTH: 23
<212> TYPE: DNA
<213> ORGANISM: Mus musculus

<400> SEQUENCE: 3

```
cttttcgcct gccttttctc ctt                                            23
```

<210> SEQ ID NO 4
<211> LENGTH: 24
<212> TYPE: DNA
<213> ORGANISM: Mus musculus

<400> SEQUENCE: 4

```
agccatggaa cagtcaaagg tcaa                                           24
```

<210> SEQ ID NO 5
<211> LENGTH: 20
<212> TYPE: DNA
<213> ORGANISM: Mus musculus

<400> SEQUENCE: 5

```
tcaggagggc caggagtcgt                                                20
```

<210> SEQ ID NO 6
<211> LENGTH: 20
<212> TYPE: DNA
<213> ORGANISM: Mus musculus

<400> SEQUENCE: 6

```
gagggccggc agggacagac                                                20
```

<210> SEQ ID NO 7
<211> LENGTH: 21

```
<212> TYPE: DNA
<213> ORGANISM: Mus musculus

<400> SEQUENCE: 7
gggggtgggg tgggtgagag g                                              21
```

METHOD OF IDENTIFICATION OF INHIBITORS OF PDE1C AND METHODS OF TREATMENT OF DIABETES

CROSS-REFERENCE TO RELATED APPLICATION

This application is a continuation of U.S. patent application Ser. No. 09/245,169, filed Feb. 5, 1999, now U.S. Pat. No. 6,417,208 B1.

STATEMENT OF GOVERNMENT INTEREST

This invention was made with government support under NIH Grant No. DRTC 9-526-1297 and American Diabetes Association grant number ADA 9-526-8900. As such, the government has certain rights in this invention.

BACKGROUND OF THE INVENTION

Diabetes is a group of diseases characterized by, among other features, defects in the regulation of glucose utilization and metabolism, resulting in impaired glucose tolerance. Despite the availability of insulin replacement therapy and a number of other therapeutic medications, which have reduced the acute mortality associated with diabetic ketoacidosis, insulin-treated patients inevitably develop long-term complications that may result in renal failure, loss of sight, as well as chronic and debilitating peripheral and cardiovascular disease. The major forms of diabetes include insulin-dependent diabetes mellitus, characterized by a deficiency of endogenous insulin secretion and non-insulin-dependent diabetes mellitus, characterized by a relative resistance of body tissues to circulating insulin. Both types of diabetes respond to administration of exogenous insulin. The various commercially available insulin preparations are protein materials that must be injected and that are associated with all of the other disadvantages that accompany the administration of foreign proteins to a patient. Previous efforts to provide oral therapeutic agents have resulted in oral hypoglycemic agents, such as the sulfonylureas, that are believed to act primarily by stimulating endogenous insulin secretion. Nevertheless, both the first and second generation sulfonylureas suffer from a number of drawbacks including hypoglycemia especially when associated with renal impairment and have been associated with a number of health risks, such as hypoglycemia and adverse effects in the cardiovascular and the central nervous system. In addition, cell replacement therapy harbors severe risks of transfer of infectious agents.

It is known that pancreatic β-cells contain several cyclic nucleotide phosphodiesterases that can be activated under different physiological conditions to lower the levels of cyclic AMP and reduce insulin secretion. Thus, it has been thought that inhibition of cyclic nucleotide phosphodiesterases of pancreatic β-cells would be a potentially powerful approach to enhancing insulin secretion in a glucose dependent fashion which also circumvents the development of the adverse effects of hypoglycemia. Pancreatic β-cells contain several cyclic nucleotide phosphodiesterases that can be activated under different physiological conditions to lower the levels of cyclic AMP and reduce insulin secretion.

For this reason, attempts have been made to identify those nucleotide phosphodiesterases that function in concert with glucose to limit insulin secretion, and which lack a strong requirement for additional hormonal or neural stimulation. Identification of such cyclic nucleotide phosphodiesterases would also provide valuable targets for the development of novel anti-hyperglycemic agents. However, to date, previous efforts to identify pancreatic β-cell phosphodiesterases relevant to glucose dependent insulin secretion have been unsuccessful. Contradictory results have been reported by several studies that implicate PDE3 in regulation of glucose dependent insulin secretion (Shafiee-Nick et al., *Br J Pharmacol.* 115:1486–92, 1995; Parker et al., *Biochem Biophys Res Commun.* 217:916–23, 1995; Leibowitz et al., Diabetes 44:67–74, 1995; Zhao et al., *Proc Natl Acad Sci USA* 94: 3223–8, 1997). Data concerning PDE4 is controversial (Shafiee-Nick et al., *Br J Pharmacol.* 115:1486–92, 1995; Parker et al., *Biochem Biophys Res Commun.* 217:916–23, 1995; Leibowitz et al., Diabetes 44:67–74, 1995; Zhao et al., Proc Natl Acad Sci USA 94: 3223–8, 1997). However, more current studies demonstrate effects of PDE3 only in the presence of hormone regulators like insulin like growth factor 1 and leptin (Zhao et al., *Proc Natl Acad Sci USA* 94:3223–8, 1997; Zhao et al., *J.Clin.Invest.* 102:869–872, 1998). Further, these studies show that PDE4 does not affect insulin secretion under these circumstances (Zhao et al., Proc Natl Acad Sci USA 94:3223–8, 1997; Zhao et al., *J.Clin.Invest.* 102:869–872, 1998). In addition, the presence of PDE3 in adipocytes and in liver and its contribution to insulin action in these tissues, make that enzyme an unsuitable target for the treatment of hyperglycemia. Accordingly, in vivo administration of PDE3 inhibitors to rats failed to affect fasting or post-glucose plasma glucose levels (El-Metwally et al., *Eur J Pharmacol.* 324:227–32, 1997, Parker et al. *Biochem Biophys Res Commun.* 236:665–9, 1997).

Complications associated with insulin administration involve the introduction of foreign proteins to patients, and with cell replacement therapy the introduction of infectious agents. Complications associated with oral hypoglycemia agents involve the uncoupling of insulin secretion from nutritional, hormonal and neural regulation, hypoglycemia and other adverse effects. For these reasons, there remains a need in the art for new agents useful in the treatment of the various types of diabetes and for new methods of identifying such agents.

Pancreatic β-cells contain multiple cyclic nucleotide phosphodiesterases that lower cAMP levels and reduce insulin secretion. Inhibition of β-cell cAMP phosphodiesterases can augment insulin secretion in a nutrient, hormone and neural sensitive fashion, and thus provide a powerful approach for regulating or increasing insulin secretion. Thus far, β-cell cyclic nucleotide phosphodiesterases that can serve as targets for regulating or increasing insulin secretion were not identified (Shafiee-Nick et al., *Br. J. Pharmacol.* 115:1486–92, 1995; Parker et al., *Biochem. Biophys. Res. Commun.* 217:916–23, 1995; Leibowitz et al., *Diabetes* 44:67–74, 1995; Zhao et al., *Proc. Natl. Acad. Sci. USA* 94: 3223–8, 1997; Zhao et al., *J. Clin. Invest.* 102:869–872, 1998; El-Metwally et al., *Eur. J. Pharmacol.* 324:227–32, 1997, Parker et al., *Biochem. Biophys. Res. Commun.* 236:665–9, 1997.

The second messengers cAMP and cGMP mediate diverse physiological responses to hormones, neurotransmitters and light. Rates of cyclic nucleotide synthesis by cyclases and of their degradation by phosphodiesterases (PDEs) regulate their cellular concentrations (reviewed in Beavo, J. A. (1995) *Physiol. Rev.* 75, 725–748 and Houslay, M. D. and Milligan, G. (1997) *TIBS* 217–224). Cyclic nucleotide PDEs have been distinguished into nine families based on their substrate affinity and specificity, their selective sensitivity to cofactors and inhibitory drugs. Cyclic nucleotide PDE families are: (1) PDE1—$Ca^{+2}$/calmodulin stimulated PDEs; (2) PDE2—cGMP stimulated PDEs; (3) PDE3—cGMP inhibited PDEs; (4) PDE4—cAMP specific PDEs; (5) PDE5—cGMP specific PDEs; (6) PDE6—photoreceptor PDEs; and (7) PDE7—higher affinity cAMP specific PDEs; (8) PDE8—cAMP specific IBMX resistant PDEs (Fisher, et al. (1998) *Biochem. Biophys. Res. Commun.* 246, 570–577; Hayashi, et al. (1998) *Biochem. Biophys. Res. Commun.* 250, 751–756; Soderling, et al. (1998) *Proc. Natl. Acad. Sci. USA* 95, 8991–8996); (9) PDE9—cGMP specific IBMX resistant PDEs (Fisher, et al. (1998) *J. Biol. Chem.* 273, 15559–15564 and Soderling, et al. (1998) *J. Biol. Chem.* 273, 15553–15558). All mammalian PDEs contain a related C-terminal domain with ~30% sequence identity between families, and N-terminal regulatory domains containing cofactor or cGMP binding sites, localization and other regulatory sequences. Both tissue and cell specific gene expression, and a variable splicing pattern, contribute to the unique and complex composition of cyclic nucleotide PDEs in mammalian cells normally containing activities derived from several families of PDEs (Beavo, J. A. (1995) *Physiol. Rev.* 75, 725–748 and Houslay, M. D. and Milligan, G. (1997) *TIBS* 217–224). PDE inhibitors that do not affect adenosine uptake and exhibit high selectivity between PDE families, and in some cases between PDE isozymes, are powerful tools for identification of PDEs involved in diverse physiological responses (Ballard, et al. (1998) *J Urol* 159, 2164–2171; Giembycz, et al. (1996) *J. Pharmocology* 118, 1945–1958; Zhao, et al. (1997) *Proc. Natl. Acad. Sci. USA* 94, 3223–3228).

Insulin secretion from pancreatic β-cells is governed by the interplay between nutritional secretagogues and regulatory hormonal and neural stimuli (Rasmussen, et al. (1990) *Diabetes* 13, 655–665; Holz, G. G. and Habener, J. F. (1992) *Trends in Biochem. Sci.* 17, 388–393; Liang, Y. and Matschinsky, F. M. (1994) *Annu. Rev. Nutr.* 14, 59–81). Glucose, the major insulin secretagogue, triggers insulin release through calcium dependent vesicular exocytosis (Rasmussen, et al. (1990) *Diabetes* 13, 655–665; Holz, G. G. and Habener, J. F. (1992) *Trends in Biochem. Sci.* 17, 388–393; Liang, Y. and Matschinsky, F. M. (1994) *Annu. Rev. Nutr.* 14, 59–81; Ashcroft, S. J. and Ashcroft, F. M. (1992) *Insulin: Molecular Biology to Pathology*, Oxford Univ. Press, New York; German, M. S. (1993) *Proc. Natl. Acad. Sci. USA* 90, 1781–1785; Newgard, C. B. and McGarry, J. D. (1995) *Annu. Rev. Biochem.* 64, 689–719; Efrat, et al. (1994) *Trends in Biochem. Sci.* 19, 535–538). The glucose signal cascade leads both to membrane depolarization and a calcium influx via to the opening of L-type voltage sensitive calcium channels, and to other effects that include release of calcium from intracellular stores (Liang, Y. and Matschinsky, F. M. (1994) *Annu. Rev. Nutr.* 14, 59–81; Takasawa, et al. (1998) *J. Biol. Chem.* 273, 2497–2500; and Kajimoto, et al. (1996) *Biochem. Biophys. Res. Commun.* 219, 941–946). Hormones and insulinotropic gut factors that stimulate cAMP synthesis strongly augment glucose induced insulin secretion (Rasmussen, et al. (1990) *Diabetes* 13, 655–665; Holz, G. G. and Habener, J. F. (1992) *Trends in Biochem. Sci.* 17, 388–393; Liang, Y. and Matschinsky, F. M. (1994) *Annu. Rev. Nutr.* 14, 59–81; and Ashcroft, S. J. and Ashcroft, F. M. (1992) *Insulin: Molecular Biology to Pathology*, Oxford Univ. Press, New York). Conversely, hormonal inhibition of insulin secretion involves reductions in cAMP levels (Zhao, et al. (1997) *Proc. Natl. Acad. Sci. USA* 94, 3223–3228; D'Ambra, et al. (1990) *Endocrinology* 126, 2815–2822; Ma, et al. (1994) *Endocrinology* 134, 42–47; Grodsky, G. M. and Bolaffi, J. L. (1992) *J. Cell Biochem.* 48, 3–11; Bolaffi, et al. (1990) *Endocrinology* 126, 1750–1755). In addition to the role cAMP plays in hormonal modulation of insulin secretion, basal cAMP levels appear to be required for glucose to induce insulin secretion (Serre, et al. (1998) *Endocrinology* 139, 4448–4454). Potentiation of glucose induced insulin secretion is evident not only upon treatment of insulin secreting cells with the insulinotropic gut factor GLP1 (glucagon-like peptide 1), but also upon treatment with reagents that stimulate cAMP signaling including membrane permeable cAMP analogs, activators of adenyl cyclase, and PDE inhibitors (Rasmussen, et al. (1990) *Diabetes* 13, 655–665, D'Ambra, et al. (1990) *Endocrinology* 126, 2815–2822; Henquin, J. C. and Meissner, H. P. (1984) *Endocrinology* 115, 1125–1134; and Holz, G. G., Leech, C. A., and Habener, J. F. (1995) *J. Biol. Chem.* 270, 17749–17757). Like GLP1, these cAMP elevating agents do not induce significant insulin secretion in the absence of glucose. Targets for cAMP action are PKA substrates such as the voltage sensitive calcium channel, GLUT2 and potentially also ion channels to which cAMP binds directly (Liang, Y. and Matschinsky, F. M. (1994) *Annu. Rev. Nutr.* 14, 59–81; Leiser, M. and Fleischer, N. (1996) *Diabetes* 45, 1412–1418; Rajan, et al. (1989) *Diabetes* 38, 874–880; Ammala, et al. (1993) *Nature* 363, 356–358; Thorens, et al. (1996) *J. Biol. Chem.* 271, 8075–8081). In addition to the potentiation of glucose and calcium dependent insulin secretion, cAMP-stimulated exocytosis via calcium independent mechanisms is evident in patch clamped cells, and the contribution of this mechanism to insulin secretion under physiological conditions remains to be determined (Leiser, M. and Fleischer, N. (1996) *Diabetes* 45, 1412–1418; and Ammala, C., Ashcroft, F. M., and Rorsman, P. (1993) *Nature* 363, 356–358). A requirement for the localization of PKA to specific sites within pancreatic β-cells via anchor proteins has been demonstrated for GLP-1 potentiation of insulin secretion (Lester, L. B., Langerberg, L. K., and Scott, J. D. (1997) *Proc. Natl. Acad. Sci. USA* 94, 14942–14947).

The involvement of cyclic nucleotide PDEs in the regulation of insulin secretion is inferred from the stimulatory effects of the non-selective PDE inhibitor isobutylmethylxanthine (IBMX) on insulin secretion from insulin secreting cell lines, from islets, and from transgenic mice expressing a constitutively activated Gsα mutant in their pancreatic β-cells (Rasmussen, et al. (1990) *Diabetes* 13, 655–665; D'Ambra, et al. (1990) *Endocrinology* 126, 2815–2822; Ma, et al. (1994) *Endocrinology* 134, 42–47; Henquin, J. C. and Meissner, H. P. (1984) *Endocrinology* 115, 1125–1134). Cyclic nucleotide PDEs present in β-cells were thus far investigated as total PDE activities of crude islet extracts and the presence of PDEs 3 and 4, and calcium sensitive PDEs, in β-cells has been inferred from these studies (Henquin, J. C. and Meissner, H. P. (1984) *Endocrinology* 115, 1125–1134). The involvement of PDE3 in glucose induced insulin secretion from pancreatic islets has been demonstrated in studies using selective PDE3 inhibitors (Henquin, J. C. and Meissner, H. P. (1984) *Endocrinology* 115, 1125–1134; Lipson, L. G. and Oldham, S. B. (1983) *Life Sci* 32, 775–780; Leibowitz, et al. (1995) *Diabetes* 46, 67–74; El-Metwally, M., Shafiee-Nick, et al. (1997) *Eur. J. Pharmacol.* 324, 227–232). The presence of PDE3B in pancreatic β-cells and its involvement in IGF-1 and in leptin mediated inhibition of insulin secretion has been demonstrated recently (Zhao, et al. (1997) *Proc. Natl. Acad. Sci.USA* 94, 3223–3228; and Zhao, A. Z., Bornfeldt, K. E., and Beavo, J. A. (1998) *J. Clin. Invest.* 102, 869–873). However, in cultured pancreatic β-cells PDE3B does not appear to play a role in insulin secretion induced by glucose in the absence of hormone regulation (Zhao, A. Z., Zhao, H., Teague, J., Fujimoto, W., and Beavo, J. A. (1997) *Proc. Natl. Acad. Sci. USA* 94, 3223–3228; and Zhao, A. Z., Bornfeldt, K. E., and Beavo, J. A. (1998) *J. Clin. Invest.* 102, 869–873).

SUMMARY OF THE INVENTION

The present invention provides for a method of identifying novel agents that increase glucose dependent insulin secretion in pancreatic islet cells as well as methods of treating diabetes using agents which have an inhibitory effect on the activity of pancreatic islet cell phosphodiesterases ("PDE") enzyme, namely PDE1C. The methods described herein are based upon the inventor's surprising discovery that inhibition of PDE1C increases glucose dependent insulin secretion.

Specifically, the present invention provides for a method of identifying therapeutic agents that act to regulate or increase the release of insulin from pancreatic islet cells. The method of identification provided herein is used to determine the effects of isozyme specific phosphodiesterase inhibitors on insulin secretion from cultured pancreatic β-cells.

Further, the present invention provides for agents that have an inhibitory effect on the activity of PDE1C in pancreatic cells. Useful compositions according to the invention include, for example, compounds of the general formula: 3-isobutyl-1-methylxanthine derivatives with substitutions at positions 2 (R1) and 8 (R2). Preferably, $R_1$ and $R_2$ are independently alkyl ($C_1$ to $C_3$), fluoroalkyl ($F_1$ to $F_3$), chloroalkyl ($Cl_1$ to $Cl_3$), aryl ($C_5$ to $C_6$), fluoroaryl ($F_1$ to $F_2$), chloroaryl ($Cl_1$ to $Cl_2$).

Also provided by the present invention is a method of treating diabetes comprising administering to a subject an amount of a PDE1C inhibitor effective to treat the type II diabetes. The inhibitor may be selected from, for example, eburnamenine-14-carboxylic acid ethyl ester (vinpocetine), 8-methoxymethyl-1-methyl-3-(2-methylpropyl)xanthine (8MM-IBMX), zaprinast (M&B 22948), 4-[3-(cyclopentyloxy)-4-methoxyphenyl]-2-pyrrolidinone (rolipram), 4-(3-butoxy-4-methoxybenzyl)-2-imidazolidinone (RO20-1724), 1,6-dihydro-2-methyl-6-oxo-(3,4'-bipyridine)-5-carbonitrile (milrinone), trequinsin (HL 725), and/or combinations thereof.

Additional objects of the present invention will be apparent from the description which follows.

BRIEF DESCRIPTION OF THE FIGURES

FIG. 1 shows fractionation of soluble cyclic nucleotide PDE activities of βTC3 cells. Ten mg soluble extract of βTC3 cells were fractionated by mono-Q FPLC. The elution profile of cAMP PDE activities (circles) and of cGMP PDE activities (diamonds) assayed at 1 μM substrate is presented. The 0–0.5 M NaCl gradient is depicted. Roman numbers indicate PDE peak numbers.

FIG. 2 shows stimulation of insulin release from βTC3 cells by glucose and cyclic nucleotide PDE inhibitors. Insulin release was measured by a radio-immunoassay after a 2 hr incubation with 16.7 mM glucose and various cyclic nucleotide PDE inhibitors at the depicted concentrations. Control incubations with inhibitors in the absence of glucose did not result in significant insulin secretion (see Methods). Error bars represent SEM. * indicates p<0.005 in comparison to 150 μM 8MM-IBMX. Assays were performed in triplicates. $IC_{50}$ values for the tested inhibitors are presented in Table II and for milrinone inhibition of PDE3 is 0.3 μM (Beavo, J. (1988) Advances in Second Messenger and Phosphoprotein Research Vol. 22, Raven Press, New York).

FIGS. 3A and 3B show the results of a kinetic analysis of PDE activities of peak I. Double reciprocal Linweaver-Burke plots and Scatchard plots (inset) derived from kinetic curves are shown. Cyclic AMP and cGMP PDE assays were performed as described in Methods. Each data point represents measurements of initial rates at a suitable enzyme dilution. A plot of a typical measurement is depicted. FIG. 3A: Cyclic AMP concentrations ranging from $2 \cdot 10^{-8}$ to $10^{-5}$ M were used to determine the kinetic curve. The calculated $K_m$ is 0.47 μM cAMP, and the calculated $V_{max}$ is 120 pmole/min·mg. FIG. 3B: Cyclic GMP concentrations ranging from $10^{-7}$ to $2 \cdot 10^{-5}$ M were used to determine the kinetic curve. Two independent kinetic curves were derived as the best fit for the measured data using the computer program Kaleidagraph. The derived $K_m$ values for the two cGMP PDE activities are: 0.25 μM and 57.5 μM cGMP, and the derived $V_{max}$ values are 60 and 400 pmole/min·mg, respectively.

FIG. 5. FIG. 5 depicts the DNA sequence of a PDE1C cDNA (SEQ ID NO:1) that confirms that PDE1C is expressed in pancreatic islet β-cells. Reverse transcriptase polymerase chain reaction was used to amplify and clone a fragment of the PDE1C mRNA common to all known PDE1C isozymes.

DETAILED DESCRIPTION OF THE INVENTION

Figure 1:
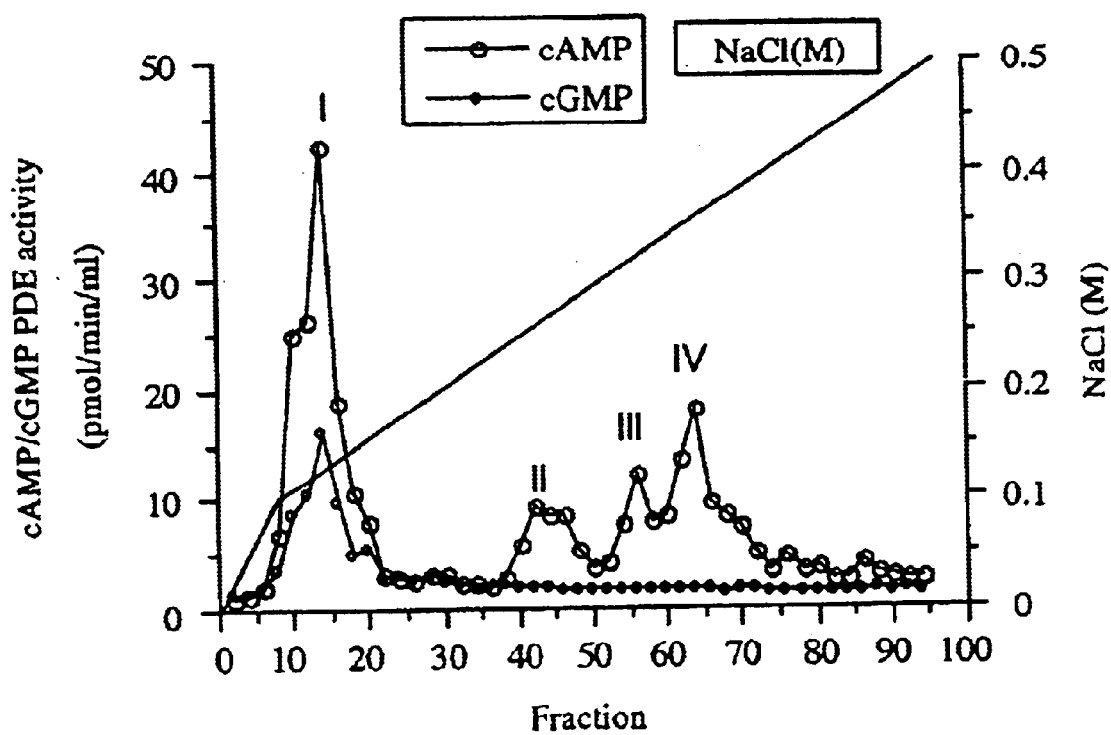
FIG. 1.

The novel method provided by the present invention allows for the isolation and identification of agents that have an inhibitory effect on the activity of phosphodiesterase. Specifically, the method provided herein involves the identification of agents that increase glucose induced insulin secretion by inhibiting the activity of PDE1C enzyme.

Specifically, the present invention provides method for identifying an agent that increases glucose dependent insulin secretion in pancreatic islet β-cells comprising the steps of: (a)obtaining a pancreatic islet β-cell culture; (b) contacting the pancreatic islet β-cell culture with an agent of interest; and (c)detecting whether said agent of interest has an inhibitory affect on the activity of phosphodiesterase 1C in said pancreatic islet β-cells, the presence of an inhibitory effect indicating that the agent of interest may be useful for increasing insulin secretion.

The inhibition to phosphodiesterase 1C activity is detected by measuring substrate concentrations of cGMP phosphodiesterase activity. Inhibition may also be determined by the assessment of glucose induced insulin secretion in the presence of selective inhibitors of cAMP phosphodiesterases of pancreatic β-cells.

The insulin secretion can be measured by any of the methods known to one of skill in the art for quantifying insulin release from cultured pancreatic cells. Preferably, radio-immunoassay methods are employed. The effects of the agent of interest, which is a potential PDE1C inhibitor compound, on phosphodiesterase activity, and on glucose stimulated insulin secretion, are determined by contacting cultured pancreatic β-cells with such potential PDE1C inhibitor compounds. The agent of interest is applied to the cultured pancreatic β-cells in a range of concentrations. These concentrations preferably range from about ten to about one hundred-fold of the IC$_{50}$ value established for the PDE1C isozyme present in pancreatic β-cells.

In a further aspect of the invention, potential PDE1C inhibitors to be screened for useful phosphodiesterase inhibitors are applied to the assay system in concentrations that range from the low and sub-micromolar range to the mid-micromolar range. Potential PDE1C inhibitors are optionally prescreened by art-known methods for inhibition of cAMP phosphodiesterase activity. Simply by way of example, potential inhibitors are prescreened in phosphodiesterase deficient yeast cells expressing the relevant mammalian phosphodiesterase isozyme (U.S. Pat. No. 5,527,896-A, incorporated herein by reference in its entirety). IC$_{50}$ values are determined in this system and in phosphodiesterase preparations from pancreatic beta-cells.

The agent of interest is applied to cultured pancreatic β-cells along with glucose. After a co-incubation for a suitable period of time with glucose and graded quantities of the candidate inhibitor, the quantity of insulin secreted into the growth media is measured by appropriate methods, e.g., by a radio-immunoassay. The range of inhibitor concentrations applied to the cells is based on assessments of IC$_{50}$ values of the inhibitors for the PDE1C isozyme of pancreatic β-cells.

The assays can be conducted with any suitable system that is capable of reporting and/or detectably reacting to changes in PDE1C isozyme activity. Thus, in general, any system that detects reversible and/or nonreversible binding to PDE1C isozyme, including, for example, naturally occurring and/or transgenic host cell systems may be employed. Such screening systems may include PDE1C, including fragments thereof, bound to bead systems suitable for detecting reversible and irreversible binding of possible PDE1C isozyme inhibitory compounds, as well as phage expression systems, to name but a few such screening systems. PDE1C detection system that include PDE1 isozyme peptide fragments would employ fragments that included, e.g., isozyme specific binding domains.

Preferably, the assays are conducted employing naturally occurring and/or transgenic or transformed host cells capable of undergoing one or more detectable changes, e.g., colorometric, cytopathic or changes in insulin expression and/or release, in the presence of effective amounts of inhibitors of PDE1C isozyme. For example, any suitably transformed eukaryotic host cells systems capable of regulating insulin expression and release under PDE1C isozyme control, may optionally be employed to screen for PDE1C isozyme inhibitory activity.

In a preferred embodiment of the invention, assays are performed using cultured insulinoma cells. These cells are preferably derived from transgenic mice selected to express the SV40 large T antigen in their pancreatic β-cells that are maintained in culture. The assay employing such cultured insulinoma cells is preferably conducted as follows.

The cultured cells are starved for glucose in Hepes buffered Krebs-Ringer solution for 1 hr. Subsequently, 16.7 mM glucose and the potential phosphodiesterase inhibitors are added to the cells in Hepes buffered Krebs-Ringer solution and the cells are incubated for 2 additional hr. Each condition is assayed in triplicate. Insulin content of the supernatant after centrifugation, and of the cells after acid extraction, is determined by a radioimmunoassay. Control samples are treated with no potential inhibitor compound or, for control or calibration purposes, with compounds that will inhibit other PDE isozymes but that are known to lack PDE1C inhibitory activity or, for examining glucose-independent effects of potential inhibitor compound alone.

To identify selective inhibitors of the specific PDE1C isozyme of pancreatic β-cells, and to determine their IC$_{50}$ values, yeast cultures expressing this enzyme or partially purified preparations of this enzyme are used to measure concentration dependent inhibition of PDE1C activity. PDE1C is partially purified by mono Q anion exchange fast performance liquid chromatography. Identified selective PDE1C inhibitors are subsequently applied to cells at concentrations ranging from 10 to 100 fold their IC$_{50}$ values for PDE1C.

In order to better describe how the methods of the invention can be employed to identify potential inhibitors of PDE1C isozyme activity, the following compounds are screened: eburnamenine-14-carboxylic acid ethyl ester (vinpocetine), 8-methoxymethyl-1-methyl-3-(2-methylpropyl)xanthine (8MM-IBMX), zaprinast (M&B 22948), 4-[3-(cyclopentyloxy)-4-methoxyphenyl]-2-pyrrolidinone (rolipram), 4-(3-butoxy-4-methoxybenzyl)-2-imidazolidinone (RO20-1724), 1,6-dihydro-2-methyl-6-oxo-(3,4'-bipyridine)-5-carbonitrile (milrinone), trequinsin (HL 725), KS505a, SCH51866, sildenafil, benzyladenine, substitutions including alkyl (C$_1$ to C$_3$), fluoroalkyl (F$_1$ to F$_3$), chloroalkyl (Cl$_1$ to Cl$_3$), aryl (C$_5$ to C$_6$), and fluoroaryl (F$_1$ to F$_2$), chloroaryl (Cl$_1$ to Cl$_2$) at position 9 of benzyladenine, and additional substitutions including alkyl (C$_1$ to C$_3$), fluoroalkyl (F$_1$ to F$_3$), aryl (C$_5$ to C$_6$), and fluoroaryl (F$_1$ to F$_2$) at positions 2 and 8 of 1-methyl-3-isobutylxanthine (IBMX), and/or combinations thereof. These compounds are tested in yeast cultures expressing the specific PDE1C isozyme of pancreatic β-cells or in partially purified preparations of this enzyme are used to measure concentration dependent inhibition of PDE1C activity.

Potential inhibitors of PDE1C activity are then tested for potentiation of insulin secretion in cultured pancreatic beta-cells, in islets, and subsequently in mammals, e.g., standard animal models for diabetes. Such inhibitors are potential therapeutic agents for intervention with the progression of type II diabetes.

The present invention further provides novel phosphodiesterase 1C inhibitors identified by the methods described herein.

Also provided by the present invention is a method of treating type II diabetes comprising administering to a subject an amount of a phosphodiesterase 1C inhibitor effective to treat the type II diabetes. The phosphodiesterase 1C inhibitor may be, for example, a compound of the general formula isobutylmethylxanthine derivatives with substitutions at positions 2 and 8. The phosphodiesterase 1C inhibitor may also be, for example, selected from the group consisting of eburnamenine-14-carboxylic acid ethyl ester (vinpocetine), zaprinast,4-[3-(cyclopentyloxy)-4-methoxyphenyl]-2-pyrrolidinone (rolipram), 1,6-dihydro-2-methyl-6-oxo-(3,4'-bipyridine)-5-carbonitrile (milrinone), and/or combinations thereof.

A major treatment method of diabetes involves the administration of exogenous insulin to patients. Complications of insulin therapy include the administration of foreign proteins and the bypass of nutrient/hormone regulation of circulating insulin levels. Type II diabetes patients with functional insulin secreting pancreatic beta-cells respond to oral hypoglycemic agents like sulfonylureas. Complications arising from use of sulfonylureas include hypoglycemia, and associated health risks and adverse effects on the cardiovascular and central nervous systems. Use of phosphodiesterase inhibitors with selectivity to the PDE1C isozyme of pancreatic beta-cells provides nutrient dependent potentiation of insulin secretion that is not associated with hypoglycemia as its effects are dependent on circulating glucose levels. Tissue and cell-specific expression pattern ensures reduced risks and side effects.

While not wishing to be bound by any theory or hypothesis as to how inhibitors of pancreatic islet cell phosphodiesterase 1C function to treat clinical diabetes, these inhibitors can be used to treat forms of diabetes that are responsive to insulin administration and wherein sufficient islet cell function remains in the mammal, e.g., a human patient, that is treated for this condition.

Of course, the artisan will appreciate that inhibitors of pancreatic islet cell phosphodiesterase 1C utilized in the treatment of diabetes will also be selected to avoid clinically undesirable side effects when administered in an amount and for a duration that is effective to achieve a therapeutic anti-diabetes effect.

The inhibitors of pancreatic islet cell phosphodiesterase 1C can be administered by any suitable art-known methods, e.g., simply by way of example, by mouth, by an intranasal and/or inhalation route of administration, by infusion into any suitable body cavity or system, by injection, including intradermal, intramuscular, intravenous and intra-arterial injection and well as by buccal, rectal and/or vaginal routes of administration.

In one embodiment of the invention, inhibitors of pancreatic islet cell phosphodiesterase 1C are administered orally, in the form of a tablets, capsules, liquids and/or powders. Optionally, a therapeutically effective amount of one or more of the inhibitor(s) are formulated together with suitable quantities and/or proportions of art-known pharmaceutically acceptable binders, fillers, excipients, gums and gels, as may be deemed suitable for achieving a desired rate of release into the gastrointestinal tract and a desired rate of absorption into the bloodstream. In another embodiment of the invention, one or more of the inhibitor(s) identified by the assays of the invention are administered in the form of a powder or mist, e.g., by inhalation and insufflation, optionally employing suitable, art known inhaler or insufflation devices. In addition, the inhibitor is optionally and conveniently incorporated into an ointment, gel, gum, paste or patch suitable for permitting one or more of the inhibitor(s) to be absorbed by a transdermal route.

In a yet another embodiment of the invention, one or more of the inhibitor(s) identified by the assays of the invention are administered in the form of an ointment, gel, paste or suppository suitable for buccal, rectal or vaginal administration.

The invention also provides for pharmaceutical compositions comprising inhibitors of pancreatic islet cell phosphodiesterase 1C administered via art-known liposomes, microparticles, or microcapsules.

Exemplary materials and methods for compounding one or more inhibitors for oral, intranasal, inhalation, transdermal, infusion/injection, buccal, rectal and/or vaginal administration are described, for example, by *Remington's Pharmaceutical Sciences*, 16th Ed., A. Osol, Ed. (1980), the disclosure of which is incorporated by reference herein in its entirety.

The artisan will appreciate that the effective dose of any particular inhibitor of pancreatic islet cell phosphodiesterase 1C that is required to achieve useful clinical results will depend upon the activity and potentency of such an inhibitor of pancreatic islet cell phosphodiesterase 1C, as well as upon the kinetics of absorption and on the blood concentrations of any particular inhibitor required to maintain phosphodiesterase 1C inhibitory concentrations in contact with the pancreatic islet cells. Irregardless, the artisan will understand that the correct dosage and frequency of administration for each phosphodiesterase 1C inhibitor is readily determined by the administration of each compound to a mammal, e.g., a test animal and/or human patient in need of such treatment, and measuring the resulting fasting blood glucose levels.

In yet a further embodiment of the invention, plural phosphodiesterase 1C inhibitors identified by the assays of the invention can also be administered in combination. Thus, two or more different inhibitors can be used in combination to achieve a desired control of diabetic glucose levels, while minimizing any untoward effects and while optimizing the kinetics of drug absorption and elimination and thus achieve the desired anti-diabetic effect.

Preferably, the phosphodiesterase 1C inhibitors identified by the assays of the invention are administered in an amount and at a rate sufficient to provide concentrations of inhibitor in contact with islet cells of a mammal to be treated that range from about 1 to about 1000 $\mu$g/Kg. Preferably, the inhibitors are administered in an amount and at a rate sufficient to provide concentrations of inhibitor in contact with islet cells of a mammal to be treated that range from about 1 to about 100 $\mu$g/Kg.

Highly selective inhibitors of the PDE1C isozyme of pancreatic beta-cells are administered to mammals in need thereof, e.g., including humans, in doses ranging from about 1 to about 1000 $\mu$g/Kg, and preferably 1 to about 100 $\mu$g/Kg. As noted above, effective dosages are determined by noting the dosages that produce optimal fasting glucose levels in the mammal so treated.

In a still further embodiment of the invention, one or more phosphodiesterase 1C inhibitor(s) identified by the assays of the invention can be used in combination with other, previously known, antidiabetic treatments. Thus, one or more of the inhibitors can be administered in combination with exogenously administered insulin, in combination with treatment with implanted viable pancreatic islet cells and in combination with other suitable anti-diabetic pharmaceutical agents, e.g., simply by way of example, sulfonylureas and biguanides are described, for example, in the *Clinical Practice Recommendations of the American Diabetes Association*, Volume 21 Supplement 1 (1998), the disclosure of which is incorporated by reference herein in its entirety.

The present invention is described in the following Experimental Details Section which is set forth to aid in the understanding of the invention, and should not be construed to limit in any way the scope of the invention as defined in the claims which follow thereafter.

Experimental Details Section

I. Materials and Methods

Mono-Q-FPLC fractionation of PDE activities. Cells were scraped and homogenized in a buffer containing 50 mM Tris 7.5, 250 mM sucrose, 5 mM $MgCl_2$, 0.2 $\mu$g/ml aprotinin, leupeptin and pepstatin, and 1 mM 4-(2-aminoethyl)benzenesulfonyl fluoride. Following a 30 min 150,000 g centrifugation, the supernatant was loaded onto a Pharmacia Mono-Q anion exchange column and PDE activities were fractionated by FPLC along a two step salt gradient. Column buffers were (A) 50 mM Tris 7.5 and (B)

50 mM Tris 7.5, 0.5 M NaCl. The gradient consisted of a 10 min increase to 0.2 M NaCl (20% B), and a 90 min increase to 0.5 M NaCl (100% B). One ml fractions were collected.

PDE assays and kinetic measurements. PDE assays were performed in duplicate as described (40). Analysis and plotting of kinetic data was performed by using the computer program kaleidagraph. The contributions of the high and low affinities cGMP PDEs of peak I to total PDE activity of this peak at a given substrate concentration were calculated using the formula:

$$V=V1+V2=Vm1 \cdot S/(Km1+S)+Vm2 \cdot S/(Km2+S).$$

Cell Culture, treatments and measurements of insulin secretion. βTC3 cells were cultured as described and early passages were maintained (D'Ambra, R., Surana, M., Efrat, S., Starr, R. G., and Fleischer, N. (1990) *Endocrinology* 126, 2815–2822). For measurements of insulin secretion cells were plated onto a 12-well culture dishes 3–4 days, and refed 16 hr, prior to the assay. On the experiment day, cells were washed in Hepes-buffered Krebs-Ringer solution, and incubated in this glucose-free solution for 1 hr. Subsequently, 16.7 mM glucose and, when relevant, PDE inhibitors were added to the cells in Hepes-buffered Krebs-Ringer solution and the cells were incubated for 2 additional hr. Each condition was assayed in triplicates. Insulin content of the supernatant after centrifugation, and of the cells after acid extraction, was determined by a radioimmunoassay as described (D'Ambra, R., Surana, M., Efrat, S., Starr, R. G., and Fleischer, N. (1990) *Endocrinology* 126, 2815–2822).

PDE inhibitors used are: IBMX—a non-selective inhibitor, 8-methoxymethyl-isobutylmethylxanthine (8MM-IBMX)—a PDE1 selective inhibitor, zaprinast—a PDE1/5/6 selective inhibitor, rolipram and RO20-1724—PDE4 selective inhibitors, milrinone and trequinsin—PDE3 selective inhibitors (1,41,42). All inhibitors applied to βTC3 cells in glucose-free Hepes-buffered Krebs-Ringer solution did not induce significant insulin release. The addition of glucose and 0.5 mM zaprinast to βTC3 cells induced secretion of 6.2% of the cellular insulin content (8% for 0.5 mM IBMX in the same group of cells) and thus, zaprinast had stimulatory effects on glucose induced insulin secretion. Addition of glucose and 0.2 mM RO20–1724 lead to secretion of 9.6% of the cellular insulin content (18% for 0.5 mM IBMX in the same group of cells) and RO20–1724 is thought to have limited effect on glucose induced insulin secretion. Addition of 30 nM trequinsin lead to secretion of 7% of the cellular insulin content (18% for 0.5 mM IBMX), and trequinsin is thought to have no effect on glucose induced insulin secretion.

Reverse transcriptase polymerase chain reaction (RT-PCR) analysis. RT-PCR analysis was performed on 5 μg of RNA prepared from βTC3 cells using Trizol (Gibco-BRL). Controls lacking reverse transcriptase were included in the reactions. To determine expression of PDE1C the following oligonucleotides were used: for RT—oligo dT; and for PCR amplification—JWPDE1C-5 5'-ACAGGGCAGAGGAGATCAAGTTT (SEQ ID NO:2); and JWPDE1C-3 5'-CTTTTCGCCTGCCTTTTCTCCTT (SEQ ID NO:3). The 408 bp PCR product was cloned and its DNA sequence was determined.

The following oligonucleotides were used for PCR amplification to determine the expression of PDE4A: JWPDE4A-5 5'-AGCCATGGAACAGTCAAAGGTCAA SEQ ID NO:4; and JWPDE4A-3 5'-TCAGGAGGGCCAGGAGTCGT (SEQ ID NO:5); and to determine the expression of PDE4D: JWPDE4D-5 5'-GAGGGCCGGCAGGGACAGAC (SEQ ID NO:6); and JWPDE4D-3 5'-GGGGGTGGGGTGGGTGAGAGG (SEQ ID NO:7). Amplification products 436 AND 470 bp long were obtained for PDE4A and D, respectively.

II. EXAMPLES

The following non-limiting examples are provided in order to illustrate the invention without limitation.

Example 1

Cyclic nucleotide phosphodiesterase inhibitors that augment insulin secretion were identified using used βTC3 insulinoma cells. For measurements of insulin secretion cells were plated onto a 12-well culture dishes 3-4 days, and refed 16 hr, prior to the assay. On the experiment day, cells were washed in Hepes-buffered Krebs-Ringer solution, and incubated in this glucose-free solution for 1 hour. Subsequently, 16.7 mM glucose and, when relevant, phosphodiesterase inhibitors were added to the cells in Hepes-buffered Krebs-Ringer solution and the cells were incubated for 2 additional hours. Each condition was assayed in triplicates. Insulin content of the supernatant after centrifugation, and of the cells after acid extraction, was determined by a radioimmunoassay.

Cyclic nucleotide phosphodiesterase inhibitors used are: isobutylmethyxanthine—a non-selective inhibitor, 8-methoxymethyl-isobutylmethylxanthine—a PDE1 selective inhibitor, $IC_{50}=7.5$ μM; zaprinast—a PDE1/5/6 selective inhibitor, $IC_{50}=4.5$ μM for PDE1C of βTC3 cells; rolipram and RO20-1724—PDE4 selective inhibitors, $IC_{50}$ of rolipram=1.5 and 50 nM to the PDE4 isozymes of βTC3 cells; milrinone and trequinsin—PDE3 selective inhibitors.

When applied to βTC3 cells in a glucose-free solution all inhibitors did not induce significant insulin release. An estimate for the ability of the inhibitors to permeate and inhibit PDEs within cells was provided by measurements of overall PDE activity in inhibitor-treated cells. These measurements provide an underestimate of the in vivo effects of the inhibitors due to inhibitor dilution, degradation, and release of inhibitor bound to PDEs, that occur during extraction, and are more pronounced in particulate fractions. A 30% inhibition of soluble cGMP PDE activities was observed with 8-methoxymethyl-isobutylmethylxanthine, and a 37% inhibition of soluble cAMP PDE activities was observed with rolipram when the inhibitors were applied at the highest concentrations used in insulin secretion assays (0.5 mM and 15 μM, respectively). Since cellular cGMP PDE activities include both PDE1 and the 8-methoxymethyl-isobutylmethylxanthine-resistant cGMP-specific PDE, and since cellular cAMP PDE activities include both PDE4 and the rolipram-resistant PDE1, these measurements demonstrated that effective inhibition of PDE1 by 8-methoxymethyl-isobutylmethylxanthine, and of PDE4 by rolipram, takes place in treated βTC3 cells.

The addition of glucose and 8-methoxymethyl-isobutylmethylxanthine (0.15 mM and 0.5 mM) lead to a dose dependent augmentation of insulin secretion (9.3% and 17.2% of the insulin content of the cells, respectively). Insulin secretion in the presence of 0.5 mM isobutylmethylxanthine was 15.2%. The effects of the PDE1-selective inhibitor 8-methoxymethyl-isobutylmethylxanthine were equivalent to those of the non-selective inhibitor isobutylmethylxanthine whose $IC_{50}$ values for the involved PDE families is in the low μM range. Inhibition of PDE4 with rolipram had partial stimulatory effects on glucose induced insulin secretion (7.9–10.7% over $10^4$ fold increase in its concentrations). As rolipram concentrations were in 300 fold inhibitor excess over the high $IC_{50}$ value we measured, the effects of rolipram appear limited to the inhibition of the highly rolipram-sensitive PDE4 isozyme and limited in its effects on insulin secretion. Inhibition of PDE3 with milrinone (up to 9 $\mu$M, $IC_{50}$=0.3 $\mu$M) did not affect insulin secretion. By contrast, inhibition of PDE1 by 8MM-IBMX exhibited a dose dependent augmentation of insulin secretion that was significant even at 20 fold excess over its $IC_{50}$ value. These analyzes demonstrated that, PDE1, but not PDE3 or 4, inhibits glucose induced insulin secretion from βTC3 cells.

These results were confirmed by use of additional phosphodiesterase inhibitors. The addition of glucose and 0.5 mM zaprinast (PDE1/5/6 inhibitor) to βTC3 cells enhanced glucose induced secretion while 0.2 mM RO20–1724 (PDE4 inhibitor) or of 30 nM trequinsin (PDE3 inhibitor) did not.

In this fashion additional compounds can be screened to identify inhibitors with selectivity to βTC3 cell-specific PDE isozymes.

Example 2

Cyclic nucleotide phosphodiesterase inhibitors that augment insulin secretion in βTC3 insulinoma cells are tested in rat and mouse pancreatic islets. In this assay PDE inhibitors are applied to isolated islets and insulin secretion to the media is measured.

Example 3

Cyclic nucleotide phosphodiesterase inhibitors that augment insulin secretion in pancreatic islets are tested in perfused pancreas, in mice and in hyperglycemic strains of mice. In this assay PDE inhibitors are applied to perfused pancreas and are injected into various strains of mice. Insulin secretion from the perfused pancreas is measured. Animals are monitored for fasting glucose blood levels.

III. Results

Cyclic nucleotide phosphodiesterases of βTC3 cells. To identify β-cell PDEs involved in the regulation of insulin secretion, cyclic nucleotide PDE families and isozymes expressed in βTC3 insulinoma cells were identified. For these purposes, soluble βTC3 cell extracts were fractionated by mono Q FPLC anion exchange chromatography and their cyclic nucleotide PDE activities profile was analyzed (FIG. 1). The PDE profile was comprised of four peaks of PDE activities: a single peak (peak I) containing both cAMP and cGMP PDE activities, and three cAMP specific PDE activity peaks (peaks II–IV). Both cAMP and cGMP PDE activities of peak I were stimulated by calcium and calmodulin at low substrate concentrations, demonstrating the presence of a high affinity isozyme of the dual specificity, calcium/calmodulin-dependent PDE1 in this peak (Table I). While kinetic analysis indicated that the cGMP PDE activity of peak I consists of two components, the cAMP PDE activity of peak I possessed kinetic properties of a single enzyme (see FIG. 3 below). These data suggest that a high affinity calcium/calmodulin-dependent PDE1 isozyme and a cGMP-specific PDE are present in peak I. PDE activities of peaks II–IV were abolished by 2.5 $\mu$M rolipram, a highly selective PDE4 inhibitor, thus demonstrating the presence of multiple PDE4 isozymes in βTC3 cells. Expression of both PDE4A and 4D in these cells was demonstrated by RT-PCR analysis (see Materials and Methods). Milrinone sensitive PDE3 activity constituted the majority of the particulate PDE activity (>70%, not shown). These observations demonstrate the presence of soluble PDE1 and 4 isozymes, of a soluble cGMP-specific PDE, and of a particulate PDE3, in βTC3 cells.

Figure 2:
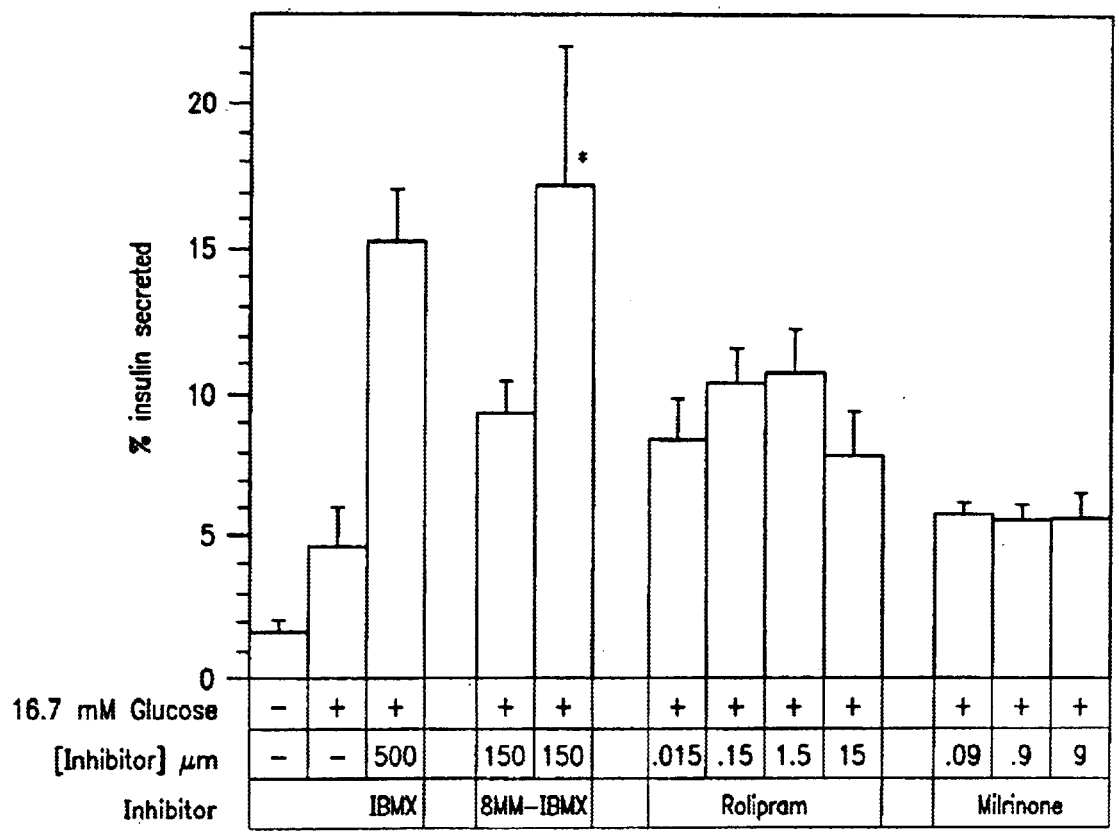
FIG. 2.

Cyclic nucleotide PDEs that counteract glucose induced insulin secretion in βTC3 cells. To identify PDEs involved in counteracting glucose induced insulin secretion, membrane-permeable, family-selective PDE inhibitors were used. These inhibitors do not affect adenosine uptake (Beavo, J. A. (1995) *Physiol. Rev.* 75, 725–748; 41. Beavo, J. (1988) *Advances in Second Messenger and Phosphoprotein Research* Vol. 22, Raven Press, New York; Wells, J. N. and Miller; J. R. (1998) *Methods Enzymol.* 159, 489–496; and Bourgignon, J. (1996) *J. Med. Chem.* 40, 1768–1770). As inhibitor $IC_{50}$ values differ among isozymes and to minimize non-specific effects of high inhibitor concentrations, inhibitor $IC_{50}$ values for βTC3 PDE isozymes were determined and applied the inhibitors to the cells at concentrations 10-100 fold above the established $IC_{50}$ values (Table II). Insulin secretion was measured by a radio-immunoassay following a two hour incubation in the presence of glucose and family selective PDE inhibitors (FIG. 2). Controls included the addition of each inhibitor and of the solvent, DMSO, in the absence of glucose (not shown). These analyses demonstrated that the PDE1 selective inhibitor 8-methoxymethyl-isobutylmethylxanthine (8MM-IBMX) strongly augmented insulin secretion in the presence of glucose, while PDE3 and PDE4 selective inhibitors did not (milrinone and rolipram, respectively). These results were confirmed (see Materials and Methods) by use of additional family selective inhibitors for PDE1 (zaprinast), PDE3 (trequinsin) and PDE4 (RO20-1724).

As observed in other insulinomas, inhibition of PDE3 did not augment glucose induced insulin secretion from βTC3 cells (Zhao, A. Z., Zhao, H., Teague, J., Fujimoto, W., and Beavo, J. A. (1997) *Proc. Natl. Acad. Sci. USA* 94, 3223–3228). Inhibition of PDE4 by rolipram had partial stimulatory effects on glucose dependent insulin secretion. However, as similar effects of rolipram were obtained along $10^4$ fold increase in its concentrations reaching a 300 fold inhibitor excess over the high $IC_{50}$ value, the inventor measured for rolipram, the effects of rolipram appear limited and restricted to the highly sensitive PDE4 isozyme present in peak IV (Table II). By contrast, inhibition of PDE1 by 8MM-IBMX exhibited a dose dependent augmentation of insulin secretion that was significant even at 20 fold excess over its $IC_{50}$ value. In this respect, the effects of this PDE1-selective inhibitor were equivalent to those of the non-selective inhibitor IBMX whose $IC_{50}$ values for the involved PDE families is in the low $\mu$M range (Beavo, J. A. (1995) *Physiol. Rev.* 75, 725–748; Beavo, J. (1988) *Advances in Second Messenger and Phosphoprotein Research* Vol. 22, Raven Press, New York; Beavo, J. A. and Reifsnyder, D. H. (1990) *Trends Pharmacol. Sci.* 11, 150–155). Thus, it appears that PDE1, but not PDE4, inhibits glucose dependent insulin secretion from βTC3 cells.

Figure 3A:
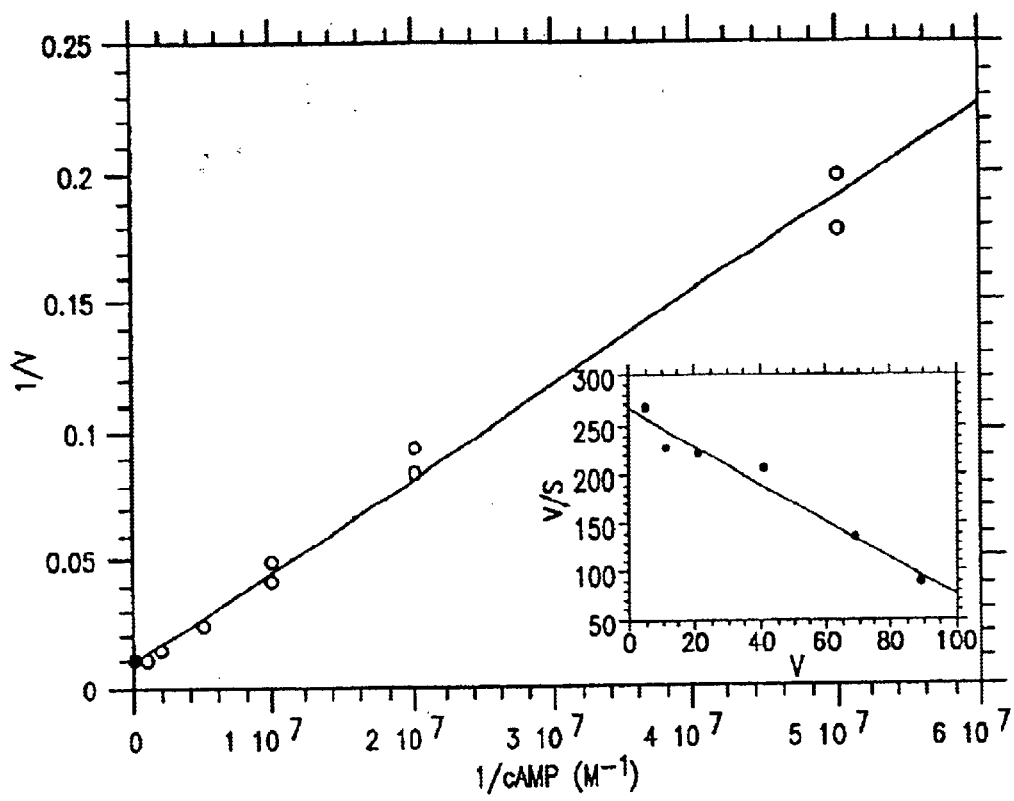
FIGS. 3A and 3B.
Figure 3B:
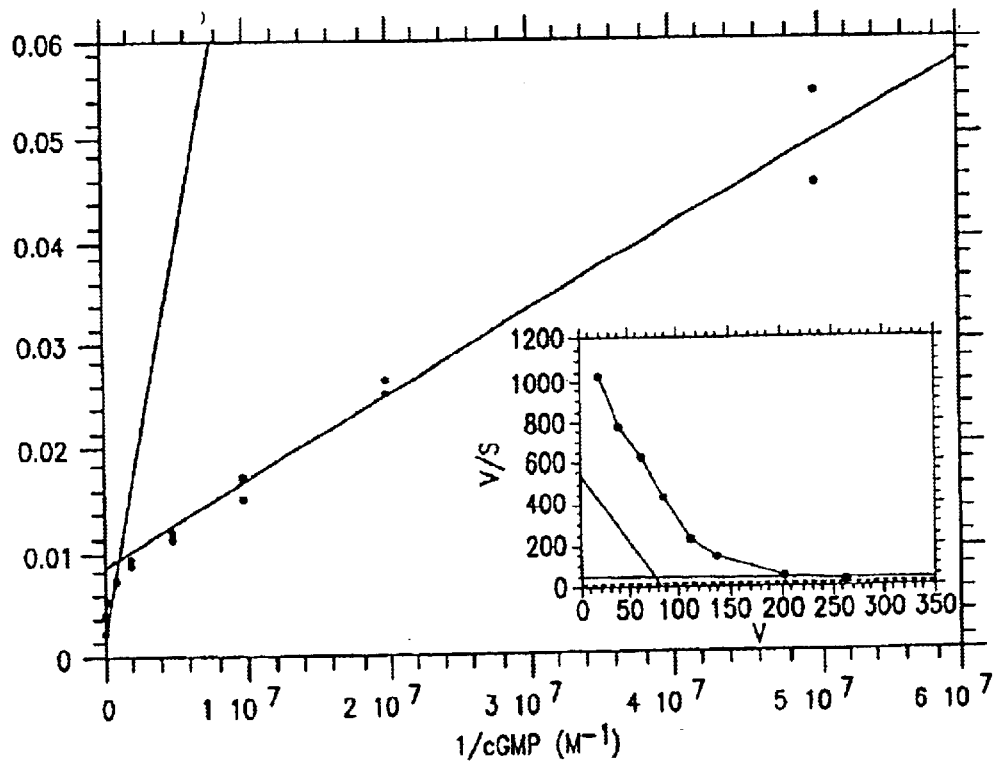

Kinetic and pharmacologic analysis of PDE activities of peak I. To identify PDE1 isozymes and other PDE activities of peak I, the inventor examined kinetic and pharmacologic properties of PDEs present in peak I (FIG. 3, Table II). Kinetics of cAMP PDE activities of peak I demonstrated the presence of a single high affinity cAMP PDE activity possessing a Km of 0.47 $\mu$M for cAMP (FIG. 3A). The kinetics of cGMP PDE activities of peak I demonstrated the presence of two cGMP PDE activities (FIG. 3B). Two kinetic curves of cGMP PDE activities resolved as the best fit for the obtained data included activities possessing Km of 0.25 $\mu$M and of 57.5 $\mu$M for cGMP. Based on these kinetic parameters, it is calculated that 95% (at 0.1 $\mu$M) and 50% (at 10 $\mu$M) of the cGMP PDE activity of peak I are derived from the high affinity PDE of this peak (see Materials and Methods). The ability of calcium/calmodulin to stimulate the high affinity cGMP PDE activity of peak I at different substrate concentrations, and the direct relationship between 8MM-IBMX inhibition and the content of the high affinity cGMP PDE activity at different substrate concentrations, strongly suggest that the low affinity cGMP PDE activity of peak I is not derived from the PDE1 isozyme present in this peak (Table I). Coupled with the sensitivity to calcium/calmodulin and to 8MM-IBMX of the cAMP PDE activity of peak I, these observations indicate that peak I, and βTC3 cells, contain a high affinity dual specificity PDE1 isozyme and a cGMP-specific PDE.

Among the three known PDE1 genes, PDE1A-C, PDE1C encoded isozymes possess high affinity cAMP and cGMP PDE activities with Km values in the range of peak I, while PDE1A and PDE1B encoded isozymes possess low affinity cAMP PDE activity with Km values ranging from 25 to 120 $\mu$M. RT-PCR analysis with oligonucleotides derived from a region common to all five known PDE1C splice variants, and determination of the DNA sequence of the amplified fragment, demonstrated the presence of PDE1C mRNA in βTC3 cells (see Materials and Methods). The pharmacologic properties of the cAMP PDE activity and of the high affinity cGMP PDE activity of peak I, are consistent with its identification as PDE1C (Table II). Unlike PDELA and 1B, PDE1C is sensitive to zaprinast and resistant to vinpocetine (Yan, C., Zhao, A. Z., Bentley, J. K., and Beavo, J. A. (1996) *J. Biol. Chem.* 271, 25699–25706; Davis, R. L. and Kiger, J. A., Jr. (1980) *Arch. Biochem. Biophys.* 203, 412–421). Accordingly, vinpocetine has been demonstrated to be an ineffective simulator of glucose induced insulin secretion while zaprinast had partial stimulatory effects on insulin secretion in our assays (Parker, J. C., VanVolkenburg, M. A., Ketchum, R. J., Brayman, K. L., and Andrews, K. M. (1995) *Biochem. Biophys. Res. Commun.* 217, 916–923), see Materials and Methods). Thus, the PDE1C isozyme present in βTC3 cells appears to down-regulate glucose induced insulin secretion.

PDE1 activity is upregulated by glucose. PDE1 activity is regulated by intracellular calcium levels and by phosphorylation. It was therefore of interest to determine whether feedback regulation of glucose induced insulin secretion involves the stimulation of PDE1C activity by glucose. To determine whether PDE1C activity is elevated upon glucose feeding, we compared the high affinity soluble cGMP PDE activity of glucose fed cells to that of glucose starved cells (Table III). PDE assays were performed at substrate concentrations calculated to be composed of >95% of the low affinity activity of PDE1C (0.1 $\mu$M). This analysis demonstrated that the PDE1C activity of glucose starved cells was consistently less responsive to the calcium/calmodulin provided in the assay mix in comparison to the PDE1C activity of glucose fed cells. Thus, the calcium/calmodulin stimulatable activity of PDE1C appeared to be elevated upon exposure to glucose. The elevations in stimulatable PDE1C activity detected in protein extracts of glucose fed cells may reflect increased PDE1C expression and/or post translational modifications that sensitize its response to calcium/calmodulin. In vivo, elevations in intracellular calcium induced by glucose, as well as increased responsiveness to calcium/calmodulin, simultaneously increase PDE1C activity upon exposure of cells to glucose.

IV. Discussion

The studies described herein detail the characterization of cyclic nucleotide PDEs of βTC3 cells and the identification of PDE1C as a regulator of glucose induced insulin secretion. Chromatographic fractionation, coupled with biochemical and pharmacologic characterization, and with RT-PCR analysis, established the presence of PDEs 1C, 4A, 4D, and of a cGMP-specific PDE, in soluble extracts of βTC3 cells. By use of family selective PDE inhibitors in concentrations that do not exceed a 100 fold excess over $IC_{50}$ values we determined for the isozymes expressed in βTC3 cells, we observed the involvement of PDE1C, and the limited involvement of PDE4 isozymes, in the regulation of insulin secretion. PDE1C activity is elevated upon exposure of cells to glucose, constituting a feedback control mechanism of glucose induced insulin secretion via increased cAMP degradation by PDE1C.

Fractionation of cellular PDE activities permits the identification of active PDEs and provides an estimate of their relative contribution to cellular PDE activity. While PDE isozymes can be identified by molecular approaches such as RT-PCR, fractionation of cellular PDE activities allows the determination of kinetic and pharmacologic properties of the specific isozymes expressed in the cells. The fractionation of βTC3 cell PDEs we undertook allowed the identification not only of βTC3 cell PDE isozymes but also of isozyme-effective inhibitors and the applicable range of concentrations for specific inhibition of a given PDE isozyme within the cell. The fractionation of βTC3 cell PDEs proved critical for detecting the involvement of PDE1C in the regulation of insulin secretion, as its inhibitor profile identified relevant and effective inhibitors that were not examined in pancreatic β-cells (Parker, J. C., VanVolkenburg, M. A., Ketchum, R. J., Brayman, K. L., and Andrews, K. M. (1995) *Biochem. Biophys. Res. Commun.* 217, 916–923; Shafiee-Nick, R., Pyne, N. J., and Furman, B. L. (1995) *Br. J. Pharmacol.* 115, 1486–1492). Previous studies in pancreatic islets suggest the involvement of PDE3, but not of PDE4, in the regulation of insulin secretion (Parker, J. C., VanVolkenburg, M. A., Ketchum, R. J., Brayman, K. L., and Andrews, K. M. (1995) *Biochem. Biophys. Res. Commun.* 217, 916–923; Shafiee-Nick, R., Pyne, N. J., and Furman, B. L. (1995) *Br. J. Pharmacol.* 115, 1486–1492). However, perhaps due to differences in its abundance in islets and in cultured pancreatic β-cells, PDE3B does not appear to counteract glucose induced insulin secretion but to mediate the inhibitory effects of IGF-1 and leptin on insulin secretion in cultured insulinoma cells (Zhao, A. Z., Zhao, H., Teague, J., Fujimoto, W., and Beavo, J. A. (1997) *Proc. Natl. Acad. Sci. USA* 94, 3223–3228; Parker, J. C., VanVolkenburg, M. A., Ketchum, R. J., Brayman, K. L., and Andrews, K. M. (1995) *Biochem. Biophys. Res. Commun.* 217, 916–923; Shafiee-Nick, R., Pyne, N. J., and Furman, B. L. (1995) *Br. J. Pharmacol.* 115, 1486–1492; Zhao, A. Z., Bornfeldt, K. E., and Beavo, J. A. (1998) *J. Clin. Invest.* 102, 869–873). Thus, our analysis is in agreement with the currently held notion that in cultured pancreatic β-cells PDE3 and 4 are not major PDEs that counteract glucose induced insulin secretion. An analysis, however, identified PDE1C as a PDE that counteracts glucose induced insulin secretion in βTC3 cells. Preliminary analysis of effects of PDE inhibitors on insulin secretion from pancreatic islets indicates strong stimulation of glucose induced insulin secretion by inhibition of PDE1, potentiation by inhibition of PDE3 and limited effects of inhibition of PDE4 on insulin secretion (unpublished observations). PDE1, thus, appears to be an inhibitor of glucose induced insulin secretion both in cultured insulinoma cells and in pancreatic islets.

Figure 4:
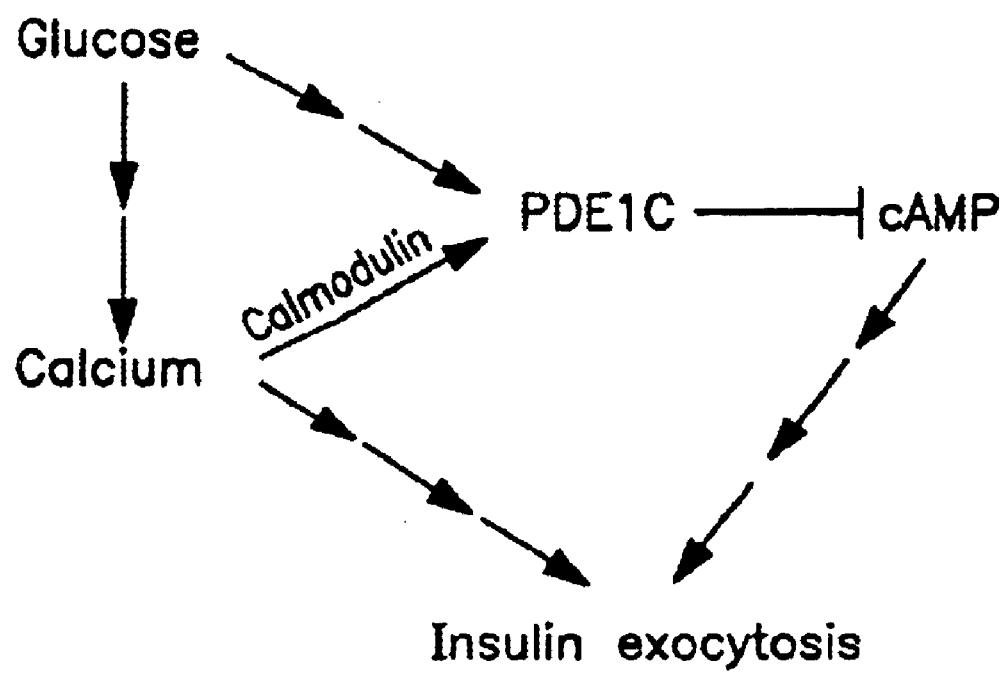
FIG. 4. Figure sets forth a model of glucose and calcium dependent feedback regulation of cAMP in βTC3 cells. Glucose triggers signaling cascades that lead to the activation of the voltage sensitive calcium channel. Cyclic AMP augments the glucose induced calcium influx and the exocytosis of vesicular insulin. PDE activity of the calcium/calmodulin dependent PDE1C is stimulated both by elevations in calcium and by additional glucose induced increases in its responsiveness to calcium/calmodulin. Increased PDE1C activity reduces intracellular cAMP concentrations and limits insulin secretion.

Unlike the limited effects of PDE4 inhibitors, inhibition of PDE1C exhibited a dose dependent stimulation of insulin secretion that can account for the stimulatory effects of non-selective inhibition of PDEs. Expression of PDE1C in pancreatic islets, detected by in situ hybridization, raises the possibility that PDE1C regulates insulin secretion from pancreatic islet β-cells too (P. H. and T. M., unpublished observations). The involvement of PDE1C in the regulation of insulin secretion, and the stimulation of its activity by glucose, suggest the existence of glucose dependent feedback control loop of insulin secretion (FIG. 4). Exposure of cells to glucose leads to increases in intracellular calcium concentrations and in vesicular exocytosis of insulin. Calcium has been proposed to activate the calcium/calmodulin dependent adenylyl cyclase of β-cells, a process that can potentiate insulin secretion. However, calcium also stimulates the calcium/calmodulin dependent PDE1C. While threshold calcium levels required for the activation of adenylyl cyclase and of PDE1C are not known, the inventor demonstrates in this study that the responsiveness of PDE1C to calcium is stimulated by glucose. The glucose dependent stimulation of PDE1C leads to reduced intracellular cAMP concentrations that limit insulin secretion, thus establishing a feedback mechanism that down-regulates glucose induced insulin secretion.

The PDE1C of βTC3 cells appears to be a novel isozyme distinguished by its predominant cAMP PDE activity and inhibitor sensitivity profile. Five different splice variants of PDE1C have been identified thus far, all sharing relatively high affinity and equipotent cAMP and cGMP PDE activities (Yan, C., Zhao, A. Z., Bentley, J. K., and Beavo, J. A. (1996) *J. Biol. Chem.* 271, 25699–25706; Davis, R. L. and Kiger, J. A.,Jr. (1980) *Arch. Biochem. Biophys.* 203, 412–421; Yan, C., Zhao, A. Z., Bentley, J. K., Loughney, K., Ferguson, K., and Beavo, J. A. (1995) *Proc. Natl. Acad. Sci. USA* 92, 9677–9681). These PDE1C isozymes exhibit differential sensitivity to several PDE inhibitors. Provided the tissue distribution of the PDE1C splice variant expressed in pancreatic β-cells is limited, it may prove to be a novel drug target for intervention with the progression of type II diabetes. As demonstrated in transgenic mice expressing a constitutively activated Gsα mutant in their pancreatic β-cells, inhibition of β-cell PDE1C will be particularly powerful in conjunction with cAMP elevating agents such as GLP1 (Rasmussen, H., Zawalich, K., Ganesan, Sh., Calle, R., and Zawalich, W. S. (1990) *Diabetes* 13, 655–665; D'Ambra, R., Surana, M., Efrat, S., Starr, R. G., and Fleischer, N. (1990) *Endocrinology* 126, 2815–2822; Ma, Y. H., Landis, C., Tchao, N., Wang, J., Rodd, G., Hanahan, D., Bourne, H. R., and Grodsky, G. M. (1994) *Endocrinology* 134, 42–47; Henquin, J. C. and Meissner, H. P. (1984) *Endocrinology* 115, 1125–1134). Efforts to clone cDNAs encoding PDE1C of pancreatic β-cells and to determine its tissue distribution pattern are underway.

Our analysis indicates that βTC3 cells contain multiple high affinity cAMP PDEs, that are both cAMP-specific (PDE4) and dual specificity PDEs (PDE1C and 3), and a low affinity cGMP-specific PDE. Among these cAMP PDEs, PDE1C appears to counteract glucose induced insulin secretion as its selective inhibition leads to a dose dependent augmentation of insulin secretion equivalent to the one observed upon use of the non-selective PDE inhibitor IBMX. Selective inhibition of PDE3B in cultured pancreatic β-cells by milrinone when assayed with limited excess over the $IC_{50}$ does not augment glucose induced insulin secretion but counteracts IGF-1 and leptin inhibition of insulin secretion (Zhao, A. Z., Zhao, H., Teague, J., Fujimoto, W., and Beavo, J. A. (1997) *Proc. Natl. Acad. Sci. USA* 94, 3223–3228; Zhao, A. Z., Bornfeldt, K. E., and Beavo, J. A. (1998) *J. Clin. Invest.* 102, 869–873). While PDE3B mediates hormone dependent inhibition of insulin secretion, PDE1C appears to mediate basal feedback regulation even in the absence of extracellular hormonal and neural signals. Thus, specific PDEs among the multiple PDEs present in βTC3 cells appear to play different and specialized roles in β-cell physiology and to regulate insulin secretion under different conditions.

TABLE I

Biochemical and Pharmacologic Properties of Fractionated PDE Activities of βTC3 Cells

| Peak | Substrate | $Ca^{+2}$ & calmoduli n/EDTA[a] | Inhibition by 8 MM-IBMX[b] | Rolipram[c] |
|---|---|---|---|---|
| I | cAMP 0.5 μM | 9.1 | 80% | — |
| I | cGMP 0.1 μM | 11.8 | 82% | |
| I | cGMP 10 μM | 13.1 | 57% | — |
| II | cAMP 1 μM | 1.5 | — | 98% |
| III | cAMP 1 μM | 1.1 | — | 97% |
| IV | cAMP 1 μM | 1.1 | — | 96% |

[a]Ratio of the PDE activity measured in the presence of 2mM $CaCl_2$ and 4 μg/ml calmodulin to the activity measured in the presence of 1 mM EGTA is presented.
[b]Percent inhibition by 50 μM 8 MM-IBMX. — indicates not determined
[c]Percent inhibition by 2.5 μM rolipram. — indicates not determined.

TABLE II

Inhibitor Effects on cAMP PDE Activities of PDE1C and PDE4 Isoenzymes

| | $IC_{50}$ values[a] | | |
|---|---|---|---|
| Compound | Peak I PDE1 | Peak II PDE4 | Peak IV PDE4 |
| 8 MM-IBMX | 7.5 ± 2 μM | — | — |
| Zaprinast | 4.5 ± 2 μM | — | — |
| Vinpocetine | >100 μM | — | — |
| Rolipram | >100 μM | 50 nM | 1.5 nM |
| Milrinone | >100 μM | — | — |

[a]$IC_{50}$ values were determined using 1 μM cAMP substrate and are presented as average ± standard deviation. — indicates not determined.

TABLE III

Glucose Effects on PDE1C Activity

| Glucose[a] | Cyclic GMP PDE Activity ratio[b] |
|---|---|
| — | 5.7 ± 1.5 |
| 0 | 14.2 ± 5.3 |

[a]Cells were starved for glucose for 1 h(−) and then incubated with 16.7 mM glucose for 1.5 h(+).
[b]Cyclic GMP PDE activity was assayed using 0.1 μM cGMP substrate at appropriate extract dilutions. Values represent the ratio of PDE activity in the presence of 2 mM $CaCl_2$ and 4 μg/ml calmodulin to the PDE activity in the presence of 1 mM EGTA. The average and standard error values are presented. Student t-value indicates significance of >99.5%.

What is claimed:

1. A method of increasing glucose dependent insulin secretion in a pancreatic β-cell in a mammal, where the mammal is in need of increased glucose dependent insulin secretion, the method comprising administering an effective amount of a selective inhibitor of phosphodiesterase 1C to the mammal.

2. The method of claim 1, wherein the inhibitor is an isobutylmethylxanthine with substitutions consisting of a moiety at positions 2 (R1) and 8 (R2) independently selected from the group consisting of an alkyl ($C_1$ to $C_3$), a flouroalkyl ($F_1$ to $F_3$), a chloroalkyl ($Cl_1$ to $Cl_3$), an aryl ($C_5$ to $C_6$), a fluoroaryl ($F_1$ to $F_2$), and a chloroaryl ($Cl_1$ to $Cl_2$).

3. The method of claim 1, wherein the inhibitor is selected from the group consisting of zaprinast, 8-methoxymethyl-1-methyl-3-(2-methylpropyl)xanthine (8MM-IBMX), and combinations thereof.

4. The method of claim 3, wherein the inhibitor is zaprinast.

5. The method of claim 3, wherein the inhibitor is 8-methoxymethyl-1-methyl-3-(2-methylpropyl)xanthine (8MM-IBMX).

6. The method of claim 1, wherein the mammal is a human.

7. The method of claim 1, wherein the inhibitor is administered in an amount effective to regulate blood sugar levels in the mammal.

8. The method of claim 1, wherein the inhibitor is administered orally.

9. The method of claim 1, wherein the inhibitor is administered in combination with an anti-diabetic agent selected from the group consisting of insulin, a sulfonylurea, and a biguanide.

* * * * *